(12) United States Patent
Luan et al.

(10) Patent No.: US 10,317,280 B2
(45) Date of Patent: Jun. 11, 2019

(54) METHOD FOR CORRECTING MEASURING-POINT-FREE TEMPERATURE COMPENSATION MODEL DURING ONLINE APPLICATION OF NEAR INFRARED SPECTRUM ANALYZER

(71) Applicant: Jiangnan University, Wuxi (CN)

(72) Inventors: Xiaoli Luan, Wuxi (CN); Zhonggai Zhao, Wuxi (CN); Fei Liu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 15/571,033

(22) PCT Filed: Dec. 4, 2015

(86) PCT No.: PCT/CN2015/096374
§ 371 (c)(1),
(2) Date: Oct. 31, 2017

(87) PCT Pub. No.: WO2017/084118
PCT Pub. Date: May 26, 2017

(65) Prior Publication Data
US 2019/0049297 A1 Feb. 14, 2019

(30) Foreign Application Priority Data
Nov. 19, 2015 (CN) .......................... 2015 1 0808346

(51) Int. Cl.
*G01N 21/359* (2014.01)
*G01J 3/02* (2006.01)

(52) U.S. Cl.
CPC ........... *G01J 3/0286* (2013.01); *G01J 3/0275* (2013.01); *G01N 21/359* (2013.01)

(58) Field of Classification Search
CPC ............................. G01J 3/0286; G01N 21/359
See application file for complete search history.

(56) References Cited

U.S. PATENT DOCUMENTS

| | | | | |
|---|---|---|---|---|
| 5,362,965 A * | 11/1994 | Maggard | .............. | G01N 21/359 250/339.12 |
| 6,341,257 B1 * | 1/2002 | Haaland | .................... | G01J 3/28 702/22 |
| 2007/0211247 A1 * | 9/2007 | Tsenkova | ............. | G01N 21/359 356/300 |

* cited by examiner

*Primary Examiner* — Maurice C Smith
(74) *Attorney, Agent, or Firm* — Na Xu; IPro, PLLC (57) ABSTRACT

The present invention relates to a non-direct measurement temperature-compensating model correction method in the on-line application of a near-infrared spectrum analyzer, which comprises: acquiring a near-infrared spectrum of each sample under different temperature levels; respectively carrying out preprocessing and principal component analysis on the acquired spectra for temperatures and to-be-measured physical property parameters; then merging the obtained spectra to generate new spectral data; using partial least squares to model the spectral data to obtain measured values at the current moment; finally, constructing an on-line recursive algorithm, and thereby on-line near-infrared measurement with a non-direct measurement temperature compensation function is fulfilled. The present invention adopts temperature as a separate latent factor variable to participate in the process of near-infrared modeling, so that when near-infrared measurement is used, by depending on the adaptability of a model to the temperature, physical property measurement under different temperatures can be carried out without direct temperature measurement information or related calculation, and thereby the created model has better universality. The on-line recursive algorithm of the present invention has better adaptability to sample temperatures and other measurement condition changes.

6 Claims, 7 Drawing Sheets

METHOD FOR CORRECTING MEASURING-POINT-FREE TEMPERATURE COMPENSATION MODEL DURING ONLINE APPLICATION OF NEAR INFRARED SPECTRUM ANALYZER

BACKGROUND OF THE INVENTION

Field of the Invention

The present invention relates to a non-direct measurement temperature-compensating model correction method in the on-line application of a near-infrared spectrum analyzer. The present invention is applicable to the on-line real-time inspection of physical property parameters susceptible to environmental temperature, such as fluid viscosity, material density, ingredient concentration, food quality, agricultural product ingredients, active ingredient contents in medicines and gasoline product quality.

Description of the Related Art

The near-infrared spectroscopy technology is a multidisciplinary modern analysis technology integrated with spectroscopy, chemometrics, computer application and so on. It is radiation-free, pollution-free and nondestructive, and can simultaneously measure a variety of ingredients. It has been successfully applied to industries, such as the agricultural industry, the food industry, the petrochemical industry, the textile industry and the pharmaceutical industry. Moreover, in order to provide relatively comprehensive, real-time sample information for production and quality inspection departments on one hand and achieve the objective of on-line monitoring and real-time control of computers on the other hand, on-line real-time automatic analysis and detection of a near-infrared spectrum analyzer provides a broad application space for the process of production, and has important significance on increasing the economic benefit and social benefit of enterprises.

However, when the near-infrared spectrum analyzer is applied in real time on line, measurement results will be affected by environmental factors. A research indicates that a change in temperature will engender the shift of a vibrational spectrum, as a result, a near-infrared spectrum measurement result under a specific temperature is only applicable to sample quality analysis under the temperature, but the effect of the on-line analysis of sample quality is not ideal, and the shortcoming greatly limits the application of the near-infrared spectrum analyzer in real-time on-line measurement technology. In order to overcome the influence of temperature on spectra during on-line application, a plurality of methods have been proposed in succession, such as rejecting spectra affected by temperature, choosing wavebands insensitive to the influence of temperature to create an analysis model, adding a temperature correction term into a model, etc. The methods can overcome the interference of temperature change on on-line measurement. However, there has been no general rule as yet to judge which method should be used under what condition, and a choice has to be made according to a specific problem. Therefore, research on a real-time on-line measurement technique with high temperature adaptability, high precision, good robustness and higher universality has become a key to determine whether the near-infrared technology can be effectively applied on line or not.

SUMMARY OF THE INVENTION

Aimed at the great influence of temperature change on near-infrared measurement during on-line physical property measurement, a method proposed by the present invention establishes an on-line recursive algorithm with a temperature compensation mechanism. A non-direct measurement temperature-compensating model correction method in the on-line application of a near-infrared spectrum analyzer which as high temperature adaptability, high precision and good robustness is provided.

In order to achieve the objective, the present invention adopts the following technical solution:

The steps of the present invention are divided into three parts. The first part is experimental design of modeling data and collection of spectra; the second part is preprocessing of near-infrared spectra and creation of correction model; and the third part is construction of on-line recursive algorithm, and thereby on-line near-infrared measurement with a non-direct measurement temperature compensation function is fulfilled.

Experimental equipment for the modeling data comprises: (1) a sample cell capable of regulating sample temperature; (2) a temperature measurer capable of displaying temperature change; (3) a near-infrared spectrum collection instrument; (4) an optical probe without obvious influence on sample temperature; (5) a computer recorder connected with the near-infrared spectrum collection instrument.

The experimental and data collection steps of the present invention are as follows:

Experimental step 1: Maximum and minimum temperature values of samples under an on-line condition are determined. A temperature range is divided into multiple level values. Normally, each temperature level should be five times greater than the resolution of the temperature measurement instrument in order to achieve effective differentiation precision.

Experimental step 2: Under a standard temperature specified by physical property measurement, original standard data of physical property parameters of all the samples are obtained.

Experimental step 3: Under the different temperature levels, near-infrared spectrum data of all the samples are collected respectively. Temperature values serve as a latent factor, so the accurate recording of the temperature values is not necessary.

The implementation step of an on-line correction algorithm with temperature as a separate latent factor variable is as follows:

Step 1: The near-infrared spectra are preprocessed with temperature patterns as a target. First-order derivative or second-order derivative operation is carried out on the original near-infrared spectra, so that first-order derivative spectra or second-order derivative spectra are generated. Here, derivative orders may be different according to the characteristics of the physical property parameters. For example, for the high-molecular, high-viscosity samples, second-order derivative is preferred. For the low-viscosity samples, first-order derivative is preferred.

Step 2: Principal component analysis (PCA) is carried out on the generated derivative spectra to reject abnormal statistical values, so that principal component patterns of all derivative spectrum data are within a degree of statistical creditability.

Step 3: The original near-infrared spectra are preprocessed with to-be-measured physical property parameter patterns as a target. The preprocessing includes superposed operation of one or more of the following algorithms: first-order derivative, second-order derivative, maximum-minimum normalization, basic bottom line correction, scattering correction, constant bias correction, etc. Here, different preprocessing algorithms are determined according to the to-be-measured physical property parameters.

Step 4: Principal component analysis (PCA) is carried out on the generated preprocessed spectra to reject abnormal statistical values, so that the principal component patterns of all preprocessed spectrum data are within a degree of statistical creditability.

Step 5: The generated derivative spectra with temperature as the target and the preprocessed spectra with the to-be-measured physical property parameters as the target are merged.

Step 6: Original analyzed values of the to-be-measured physical property parameters under a specified temperature are taken as a predictive variable and the wave numbers of the preprocessed spectra and the wave numbers of the derivative spectra are taken as independent variables. A partial least squares algorithm (PLS) physical property parameter correction model is used:

$$P = B_1 y_1 + B_2 y_2 + L\ B_n y_n + A_1 x_1 + A_2 x_2 + L\ A_n x_n$$

here, P is a measured value of a physical property variable under a specified temperature, $B_i$, $A_i$, i=1, 2, L n are regression coefficients, and $y_i$ and $x_i$ are values of the preprocessed spectra and the derivative spectra at wave numbers i=1, 2, L n.

Step 7: New near-infrared spectrum data sets are obtained on line, and a following method is utilized to construct a recursive correction algorithm:

(1) The result obtained in step 6 is adopted as a current value P(k);

(2) The next step of measurement is calculated: $P_r(k+1) = P(k) + K[L(k-1) - P(k-1)]$;

(3) A current corrected predicted value $P_r(k)$ is assigned to the measured value P(k−1) of the previous moment, the steps are repeated, and recursive assignment operation is carried out.

Here, $P_r(k)$ is a current temperature-compensated corrected near-infrared measured physical property value, P(k−1) is an uncorrected near-infrared measured physical property value in the previous step, L(k−1) is an actual physical property parameter value used in previous calculation, and K is a correction factor or a low-order filter.

In step 7, the correction factor or low-order filter can be more general statistical judgment and logic judgment or a combination of both.

In step 7, in each step of calculation, a used physical property parameter correction model can be regenerated by updated spectrum data. The whole calculation algorithm forms a recursive form.

The present invention adopts temperature as a separate latent factor variable to participate in the process of near-infrared modeling, so that when near-infrared measurement is used, by depending on the adaptability of a model to the temperature, physical property measurements under different temperatures can be carried out without direct temperature measurement information or related calculation, and thereby the created model has better universality. The recursive algorithm of the present invention has better adaptability to sample temperatures and other measurement condition changes.

DETAILED DESCRIPTION

Example 1

Taking the measurement of the viscosity of a high-molecular compound as an example, a specific implementation method is described below. The embodiment does not limit the scope of the present invention.

Figure 12:
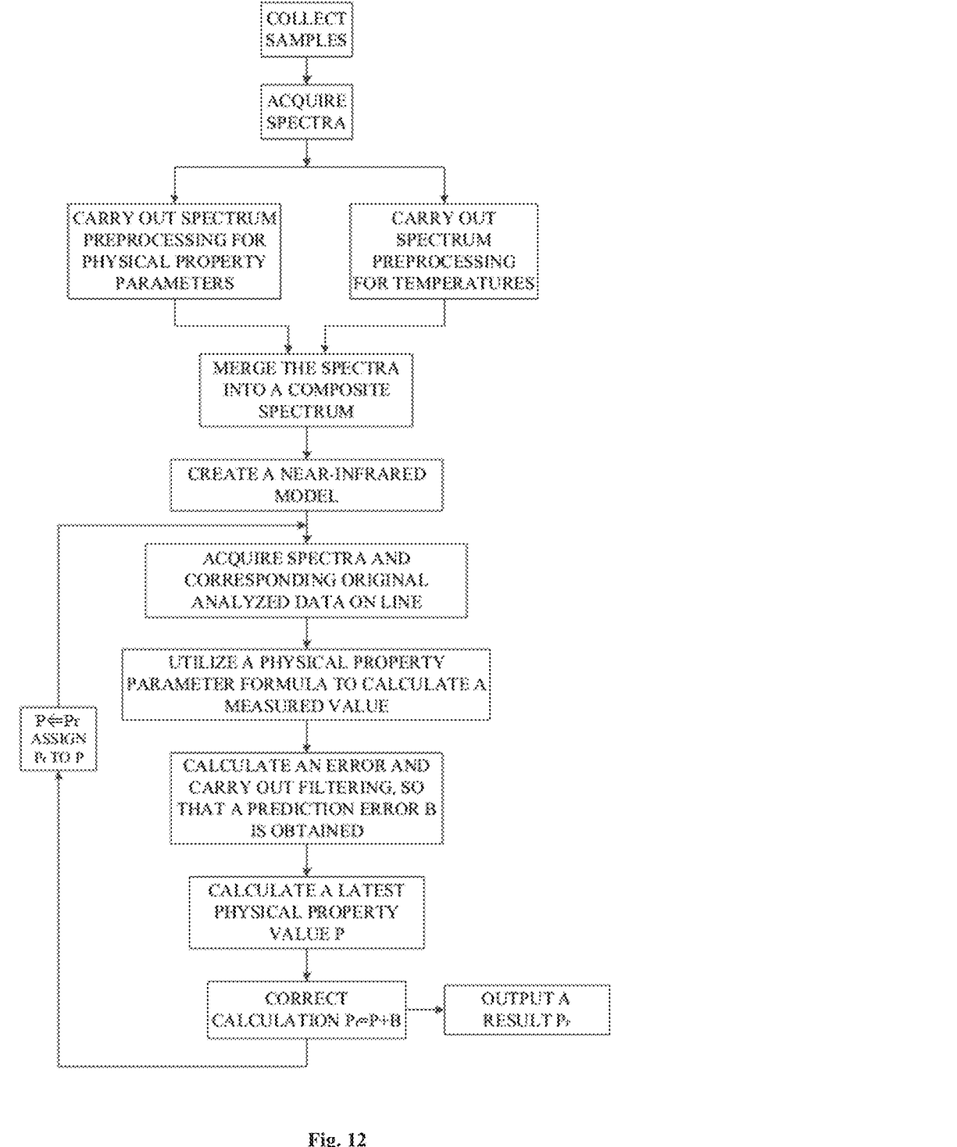
FIG. 12 is a block diagram of recursion implementation steps of a non-direct measurement temperature compensation method.

A block diagram of the whole implementation step is shown in FIG. 12.

Step 1: Representative samples are collected, and it must be ensured that to-be-measured physical property parameters of the samples can cover a range required by measurement. The total number of the samples is 40 to 60.

Figure 1:
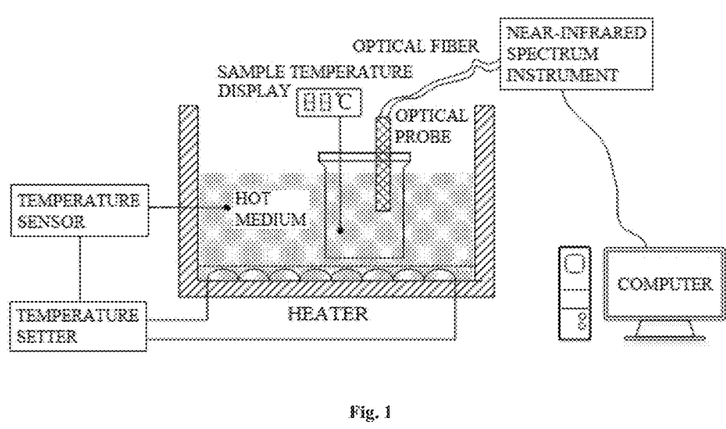
FIG. 1 is a schematic diagram of a non-direct measurement temperature-compensating experimental device.
Figure 2:
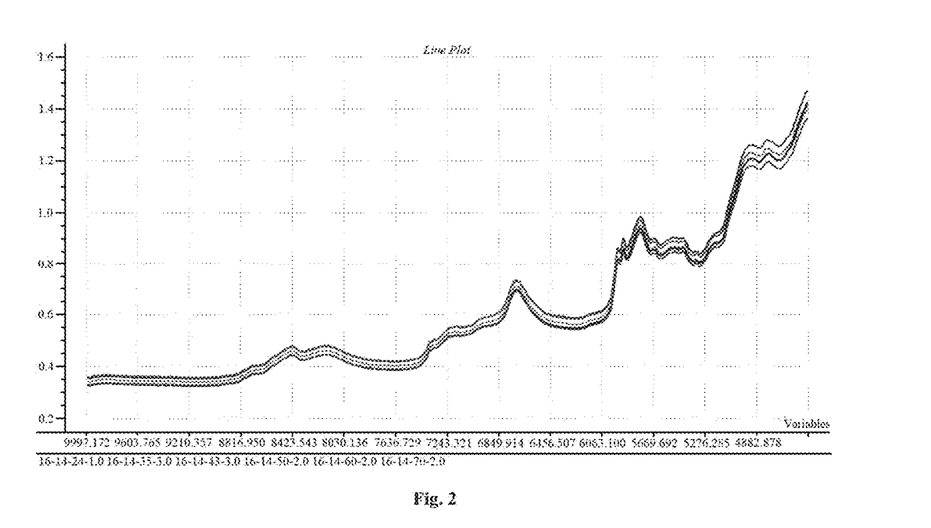
FIG. 2 is a diagram of original spectra of a high-molecular polymer under different temperatures.

Step 2: Lab equipment shown in FIG. 1 is utilized to respectively acquire near-infrared spectra of each sample under five different temperature levels, namely, 24° C., 35° C., 50° C., 60° C. and 70° C., and meanwhile, experimental conditions, such as temperature, are recorded. Acquired original spectra are shown in FIG. 2.

Figure 3:
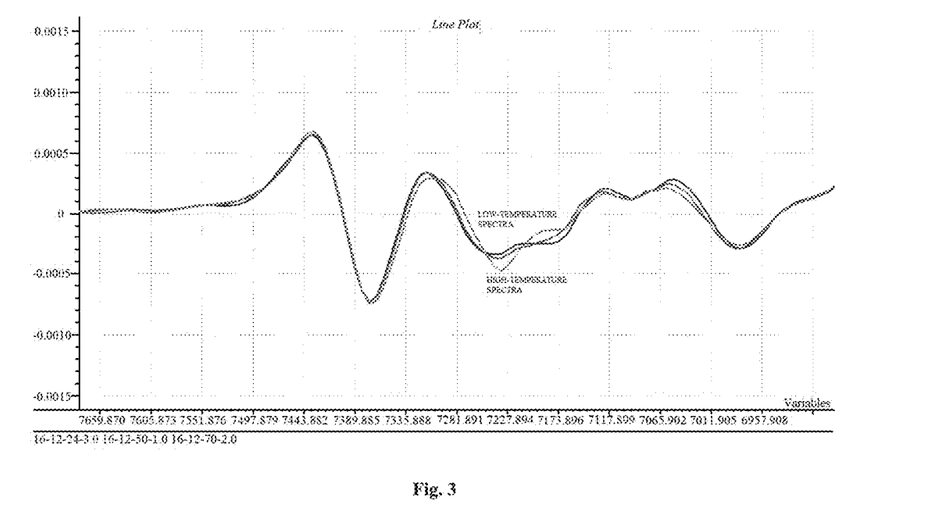
FIG. 3 is a diagram of second-order derivative-based partial spectra of a high-molecular polymer.
Figure 4:
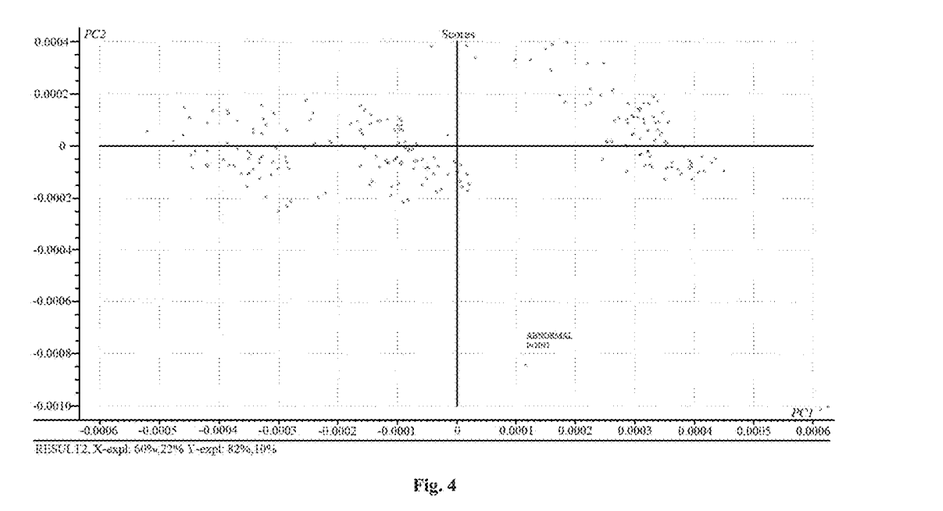
FIG. 4 is a diagram of principal component patterns of a high-molecular polymer.

Step 3: Preprocessing and principal component analysis (PCA) are carried out on the acquired spectra with temperatures as a target. Derivative spectrum data is generated. In the embodiment, second-order derivative processing and principal component analysis are carried out on the high-molecular, high-viscosity samples. On the basis of first-order derivative, second-order derivative preprocessing carries out reextraction on the spectra sensitive to temperature information, so that the overlapping of modeling wave numbers of the temperatures and the physical property parameters is reduced effectively. The processing effect is shown in FIG. 3, the fluctuation of the processed spectra caused by factors, such as light source aging, probe vibration and the degree of contact between the probe and the samples, is eliminated, and moreover, effective information of influence of the temperatures on the peak values and shapes of the spectra is kept as well. Principal component patterns are shown in FIG. 4. In the diagram of the PCA patterns shown in FIG. 4, there is a point (representing a section of spectrum) is far away from all the other points, this point is called a singular point, and is rejected during modeling, and thereby the principal component patterns of all preprocessed spectrum data are within a degree of statistical creditability.

Figure 6:
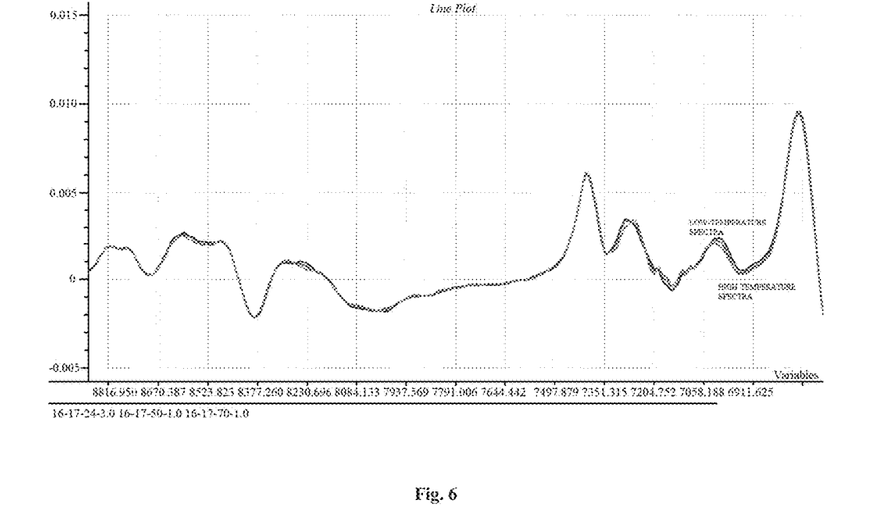
FIG. 6 is a diagram of first-order derivative-preprocessed partial spectra of a high-molecular polymer.
Figure 7:
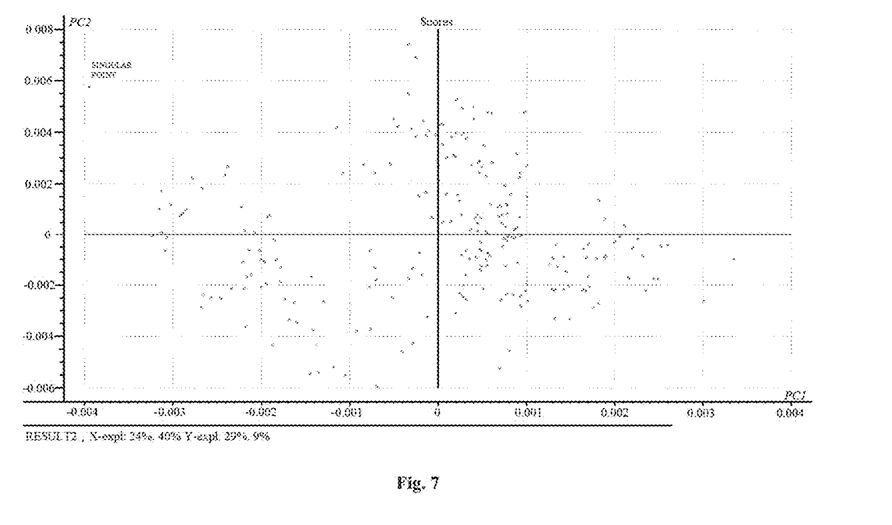
FIG. 7 is a schematic diagram of principal component analysis and abnormal pattern points of a high-molecular polymer.

Step 4: Preprocessing and principal component analysis (PCA) are carried out on the original spectra with the to-be-measured physical property parameter patterns as a target. Preprocessed spectrum data is generated. In the embodiment, first-order derivative preprocessing and principal component analysis are carried out on the high-molecular samples. The reason why the first-order derivative preprocessing is used is described in step 3. The preprocessed spectra are shown in FIG. 6, the principal component patterns are shown in FIG. 7, and there is a singular point in FIG. 7, which should be rejected, not participating in modeling anymore.

Figure 5:
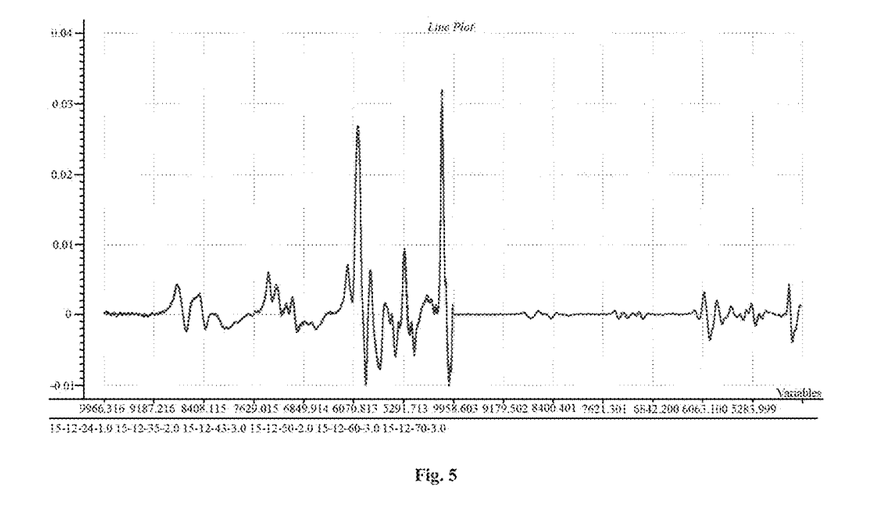
FIG. 5 is a diagram of a merged spectrum of a high-molecular polymer.

Step 5: The generated derivative spectra and the generated preprocessed spectra are merged, so that merged spectrum data is generated. FIG. 5 is a merged spectrum under different temperatures. In the merged spectrum in FIG. 5, the left half part is a first-order derivative part, which provides effective physical property modeling spectrum information; and the right half part is a second-order derivative part, which provides temperature-compensated spectrum information.

Figure 8:
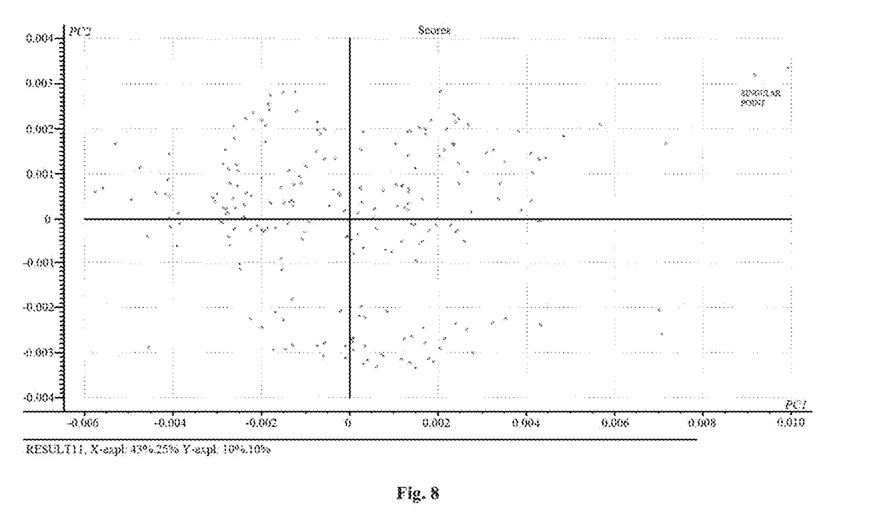
FIG. 8 is a diagram of PCA patterns of a merged spectrum of a high-molecular polymer.

Step 6: Principal component analysis (PCA) is carried out on the generated merged spectrum to reject abnormal statistical values, so that the principal component patterns of all the merged spectrum data are within a degree of statistical creditability. FIG. 8 is a diagram of PCA patterns of the merged spectrum, and in FIG. 8, there is a singular point, which should be rejected, not participating in modeling anymore.

Step 7: With original analyzed values of the to-be-measured physical property parameters as a predictive variable and the wave number of the merged spectrum as an independent variable. A partial least squares algorithm (PLS) is used for creating a physical property parameter prediction model at the current moment:

$$P = B_1 y_1 + B_2 y_2 + L\ B_n y_n + A_1 x_1 + A_2 x_2 + L\ A_n x_n$$

here, P is a measured value of a physical property variable under a specified temperature at the current moment, $B_i$, $A_i$, i=1, 2, L n are regression coefficients, and $y_i$ and $x_i$ are values of the preprocessed spectra and the derivative spectra at wave numbers i=1, 2, L n.

Step 8: Ten new spectrum data sets are acquired on line, and meanwhile, corresponding original lab data is acquired.

Step 9: Errors E(k)=L(k)−P(k) of the past ten samples are calculated, and an error time sequence
E(k−1), E(k−2), L E(k−10) is generated.

Step 10: Low-pass dynamic filtering operation is carried out on the error time sequence, so that a on-step predicted value, which is recorded as B, is obtained.

Step 11: A corrected measured viscosity value is calculated: $P_r = P + B$

Here, P is a current temperature-compensated near-infrared measured physical property value.

Step 12: The current corrected value $P_r(k)$ is assigned to the measured value P(k−1) of the previous moment, and recursive assignment operation is carried out.

Steps 8-12 are repeated.

Figure 9:
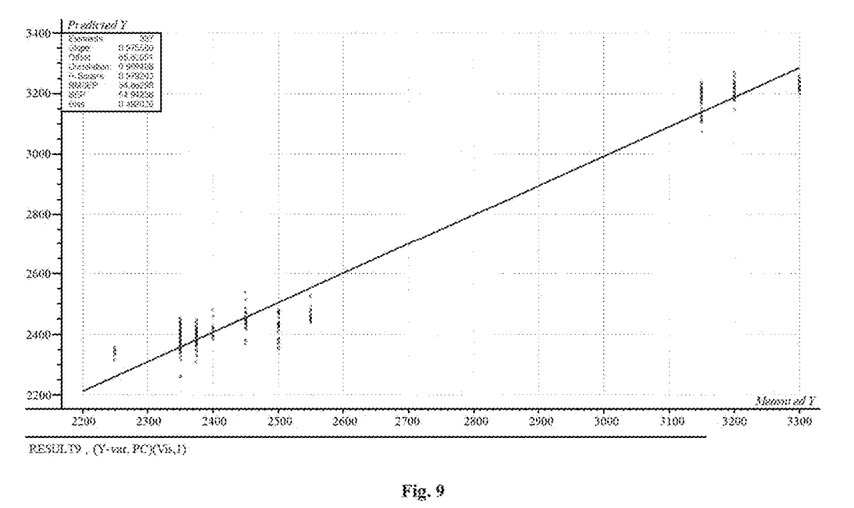
FIG. 9 is a diagram of a viscosity model generated by a merged spectrum.
Figure 10:
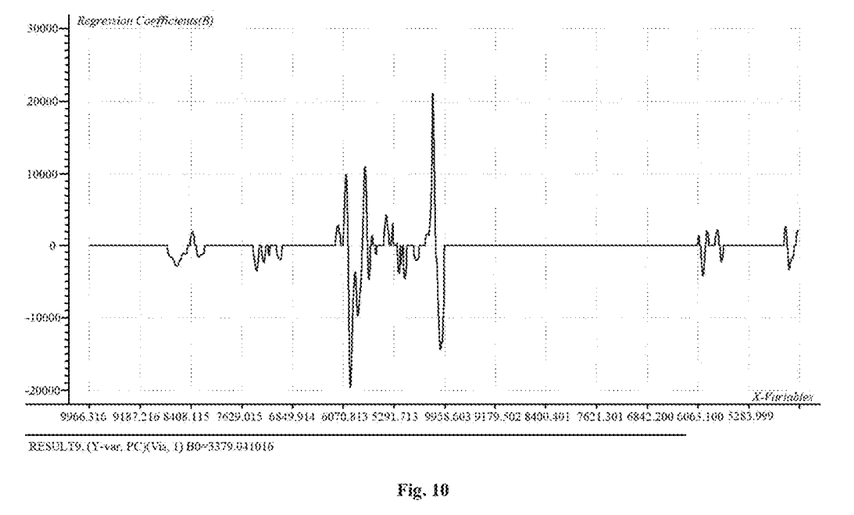
FIG. 10 is a diagram of a wave number used by a merged spectrum model.
Figure 11:
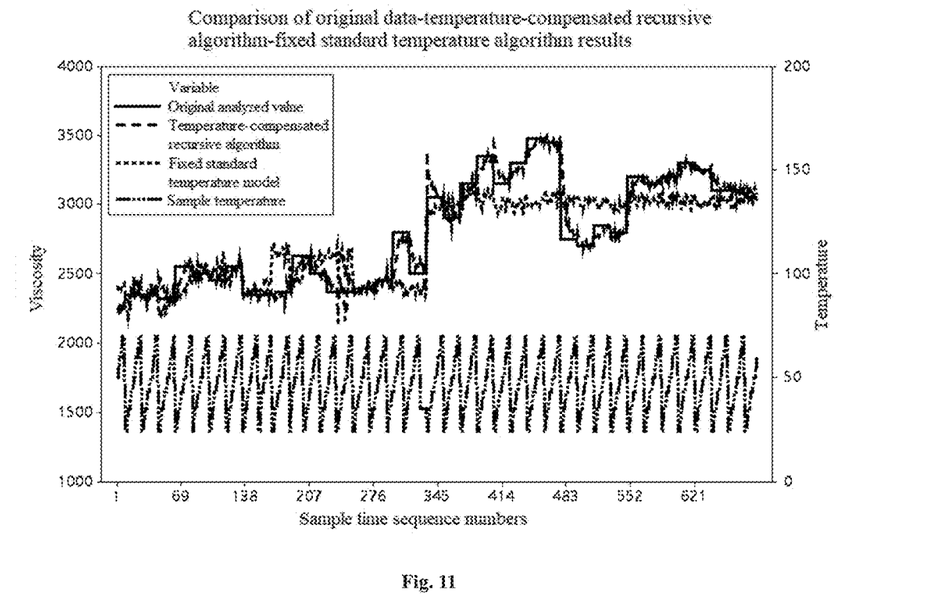
FIG. 11 is a diagram of comparison between implementation results of on-line recursion with non-direct measurement temperature compensation.

FIG. 9 is a viscosity model generated by the merged spectrum, FIG. 10 is a wave number used by the model, and FIG. 11 is an example of comparison between results of different algorithms. A waveband range shown in FIG. 10 is chosen, and two sections of first-order derivative spectrum wavelengths, which are 8909-7683 $cm^{-1}$ and 7598-4758 $cm^{-1}$ respectively, and a second-order derivative spectrum wavelength, which is 6078-4528 $cm^{-1}$, are chosen for modeling, so that FIG. 9 is obtained. It can be seen from FIG. 9 that the correlation between the predicted value of a composite spectrum model and an actual measured value is 0.99, and model precision $R^2$ is 0.98. FIG. 11 is the comparison between a non-direct measurement temperature compensation algorithm provided by the present invention and a modeling algorithm under the fixed temperature of 50° C. It can be seen from the drawing that a measurement result of a fixed-temperature model is highly sensitive to temperature change, while a model created by the method of the present invention has a better compensation effect on temperature, and moreover, because of the characteristics of a recursive algorithm, overall real-time measurement can be better in line with real analyzed data.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method comprising:
   step 1: acquiring original standard data of physical property parameters of a plurality of samples, and acquiring a near-infrared spectrum of each sample under different temperatures;
   step 2: carrying out derivative operation and principal component analysis on the near-infrared spectra acquired in step 1 with temperature as a target to reject abnormal values, and generating derivative spectra; and carrying out preprocessing and principal component analysis on the near-infrared spectra acquired in step 1 with to-be-measured physical property parameters as a target, and generating preprocessed spectra;
   step 3: carrying out spectrum merging on the derivative spectra and the preprocessed spectra generated in step 2, and generating merged spectrum data;
   step 4: carrying out abnormal statistical value rejection process on the merged spectrum data generated in step 3;
   step 5: with original standard data of the to-be-measured physical property parameters as a predictive variable and a wave number of the merged spectrum data as an independent variable, creating a physical property parameter prediction model to acquire measured values of the to-be-measured physical property parameters under a specified temperature at a current moment; and
   step 6: acquiring new near-infrared spectrum data sets on line, and correcting the measured values of the to-be-measured physical property parameters by using an on-line recursive correction algorithm.

2. The method according to claim 1, wherein a temperature range in the acquisition of near-infrared spectra of the samples in step 1 covers a real-time physical property parameter measurement temperature range; and the to-be-measured physical property parameters of the samples cover a range required by measurement.

3. The method according to claim 1, wherein the derivative operation in step 2 comprises carrying out first-order derivative operation or second-order derivative operation on the near-infrared spectra.

4. The method according to claim 1, wherein the preprocessing in step 2 comprises superposed operation of one or more of the following algorithms: first-order derivative, second-order derivative, maximum-minimum normalization, basic bottom line correction, scattering correction and constant bias correction.

5. The method according to claim 1, wherein creating the physical property parameter prediction model in step 5 comprises, adopting a partial least squares algorithm to carry out linear regression with temperature as a latent variable.

6. The method according to claim 1, wherein the on-line recursive correction algorithm in step 6 is as follows:

$$P_r(k+1)=P(k)+K[L(k-1)-P(k-1)]$$

wherein $P_r(k)$ is a temperature-compensated measurement corrected value at the current moment, $P(k-1)$ is a measured value at a previous moment, $L(k-1)$ is an actual physical property reference value used in previous calculation, and K is a correction factor or a low-order filter.

\* \* \* \* \*